United States Patent [19]

Kabbe et al.

[11] Patent Number: 4,659,737

[45] Date of Patent: * Apr. 21, 1987

[54] SUBSTITUTED AMINOMETHYL BENZOPYRANS HAVING ANTI-HYPERTENSIVE ACTIVITIES

[75] Inventors: Hans-Joachim Kabbe, Leverkusen; Ulrich Niewöhner, Wermelskirchen; Arno Widdig, Odenthal; Andreas Knorr, Wuppertal; Bernward Garthoff, Hilden; Stanislav Kazda, Wuppertal, all of Fed. Rep. of Germany

[73] Assignee: Bayer Aktiengesellschaft, Leverkusen, Fed. Rep. of Germany

[*] Notice: The portion of the term of this patent subsequent to Jan. 7, 2003 has been disclaimed.

[21] Appl. No.: 715,434

[22] Filed: Mar. 25, 1985

[30] Foreign Application Priority Data

Mar. 31, 1984 [DE] Fed. Rep. of Germany ....... 3411993

[51] Int. Cl.[4] ................ A61K 31/355; A61K 31/495; C07D 311/58; C07D 405/46
[52] U.S. Cl. .................... 514/456; 549/407; 549/362; 549/345; 548/407; 548/525; 548/526; 546/270; 546/269; 546/15; 544/377; 544/376; 514/452; 514/422; 514/409; 514/338; 514/337; 514/255
[58] Field of Search ............ 549/407, 345, 362; 514/456, 337, 338, 409, 422, 452, 255; 544/376, 377; 548/407, 525, 526; 546/269, 270, 15

[56] References Cited

U.S. PATENT DOCUMENTS 4,563,458 1/1986 Widdig et al. .................. 549/407

FOREIGN PATENT DOCUMENTS 3300004 7/1984 Fed. Rep. of Germany ...... 549/407

OTHER PUBLICATIONS

Daiichi, Chem. Abstr., 101, 191691n, (1984)–Abstract of Japan Kokai Tokkyokoho, JP59,110,690, 6/26/84.

Primary Examiner—Nicky Chan
Attorney, Agent, or Firm—Sprung Horn Kramer & Woods

[57] ABSTRACT

Substituted benzopyrans of the formula

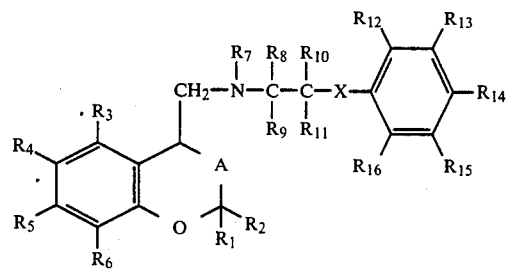

in which

—A— is a single or double bond,

X is a direct bond, optionally substituted methylene, oxygen or optionally substituted —NH—, and the various other radicals can have various meanings, or pharmaceutically acceptable addition salts thereof, which possess anti-hypertensive activity.

15 Claims, No Drawings

SUBSTITUTED AMINOMETHYL BENZOPYRANS HAVING ANTI-HYPERTENSIVE ACTIVITIES

The present invention relates to substituted benzopyrans, several processes for their preparation, and their use in medicaments, in particular in agents which influence the circulation.

The new compounds can be represented by the following formula (I):

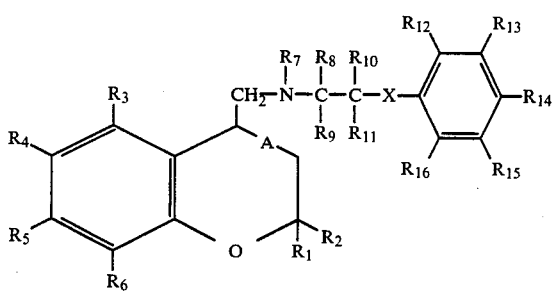

in which —A— represents a single bond or a double bond, $R_1$ and $R_2$ are identical or different and represent hydrogen, alkyl, cycloalkyl, optionally substituted aryl or optionally substituted aralkyl,
or in which
 $R_1$ and $R_2$, together with the carbon atom between them, form a carbocyclic ring,
 $R_3$, $R_4$, $R_5$ and $R_6$ are identical or different and represent hydrogen, hydroxyl, halogen, alkyl, cycloalkyl, optionally substituted aryl, optionally substituted aralkyl, alkoxy, optionally substituted aryloxy and optionally substituted aralkoxy,
 $R_7$, $R_8$, $R_9$, $R_{10}$ and $R_{11}$ are identical or different and represent hydrogen or alkyl,
 X represents a single bond or methylene which is optionally substituted by one or two alkyl groups, or represents oxygen or $NR_{17}$,
wherein
 $R_{17}$ represents hydrogen and alkyl having up to 6 carbon atoms, or
 $R_{17}$ together with $R_7$ represents $C_2$-$C_3$alkylene,
 $R_{12}$, $R_{13}$, $R_{14}$, $R_{15}$ and $R_{16}$ are identical or different and each represent hydrogen, hydroxyl, halogen, alkyl, cycloalkyl, alkoxy, aralkoxy or trifluoromethyl, and at least one and at most two of these substituents $R_{12}$-$R_{16}$ are identical or different and each represent nitro, cyano or the

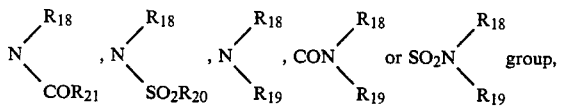

wherein $R_{18}$ and $R_{19}$ are identical or different and each represent hydrogen or optionally substituted alkyl, and wherein $R_{20}$ represents optionally substituted alkyl, and wherein
 $R_{21}$ represents hydrogen, optionally substituted alkyl, optionally substituted alkoxy or optionally substituted alkylamino, and
 $R_{12}$ and $R_{13}$ or $R_{13}$ and $R_{14}$ together each optionally represent an alkylenedioxy group or the group —CH=CH—CH=CH—, or wherein
 $R_{18}$ together with $R_{19}$ or together with $R_{20}$ or together with $R_{21}$ can form a 5-membered to 7-membered heterocyclic ring which contains an alkylene bridge having 2 to 5 carbon atoms and optionally also contains an additional carbonyl group, and their pharmaceutically acceptable addition salts.

Preferred alkyl radicals in the substituents $R_1$-$R_{21}$ are straight-chain or branched $C_1$-$C_{18}$-alkyl radicals, preferably $C_1$-$C_{12}$-alkyl radicals, in particular $C_1$-$C_6$-alkyl radicals, unless stated otherwise in the text.

The following may be mentioned as examples of alkyl radicals: methyl, ethyl, propyl, isopropyl, butyl, isobutyl, tert.-butyl, hexyl, 2-hexyl, 1,1-dimethylpentyl, 1,1-dimethylhexyl, nonyl, decyl, undecyl and tetradecyl.

Preferred cycloalkyl radicals in the radicals $R_1$, $R_2$, $R_3$, $R_4$, $R_5$, $R_6$ and $R_{12}$ to $R_{16}$ are those having 3–18, preferably 4–12, particularly preferably 5 and 6, carbon atoms, such as, for example, cyclopropyl, cyclobutyl, cyclopentyl, cyclohexyl, cycloheptyl, cyclooctyl, cyclododecyl, cycloheptadecyl and cyclooctadecyl, particularly preferably cyclopentyl and cyclohexyl.

Preferred optionally substituted alkyl radicals in the radicals $R_{12}$-$R_{21}$ are alkyl groups which are monosubsituted, disubstituted or trisubstituted by hydroxyl, halogen, in particular fluorine or chlorine, cyano, nitro, alkoxy having 1 to 4C atoms or trifluoromethoxy.

Optionally substituted aryl radicals in the radicals $R_1$, $R_2$ and $R_3$ to $R_6$ are aryl having preferably 6 to 10 carbon atoms in the aryl part. Optionally substituted phenyl and naphthyl may be mentioned as examples.

Preferred optionally substituted aralkyl radicals in the radicals $R_1$, $R_2$ and $R_3$ to $R_6$ are those which have 7 to 18 carbon atoms and the aliphatic part of which contains 1 to 8, preferably 1 to 4, carbon atoms, and the aromatic part of which is a carbocyclic radical having 6 to 10 carbon atoms. The following aralkyl radicals may be mentioned as examples: benzyl, phenylethyl, phenylpropyl, phenylbutyl or naphthylmethyl, preferably benzyl.

Alkoxy in the radicals $R_3$ to $R_6$ and $R_{12}$ to $R_{21}$ is straight-chain or branched alkoxy having preferably 1 to 6, in particular 1 to 4, carbon atoms. Methoxy, ethoxy, n- and i-propoxy and n-, i- and t-butoxy may be mentioned as examples. Aryloxy groups $R_3$ to $R_6$ and $R_{12}$ to $R_{16}$ which may be preferably mentioned are those having 6 or 10 carbon atoms, such as phenoxy or naphthyloxy.

Aralkoxy radicals having preferably 7 to 10 carbon atoms, such as benzyloxy, phenylethoxy, phenylpropoxy, phenylisopropoxy, phenylbutoxy and phenylisobutoxy, may be mentioned as aralkoxy radicals in the radicals $R_3$ to $R_6$.

Flourine, chlorine, bromine and iodine, preferably fluorine, bromine and chlorine, may be mentioned as halogens in the radicals $R_3$ to $R_6$ and $R_{12}$ to $R_{21}$.

If the radicals $R_1$ and $R_2$, together with the carbon atom between them, form a carbocyclic ring 3-membered to 12-membered rings, preferably 4-membered to 7-membered rings, are suitable. The following may be mentioned as examples of carbocyclic radicals: cyclopropane, cyclobutane, cyclopentane, cyclohexane, cycloheptane, cyclononane, cyclodecane and cyclododecane.

Suitable substituents of the aryl, aralkyl, aryloxy and aralkoxy radicals $R_1$ to $R_6$ are substituents which are not changed under the reaction conditions. The halogens, such as fluorine, chlorine, bromine and iodine, the $C_1$–$C_6$-alkyl group, the $C_1$–$C_6$-alkoxy group and the trifluoromethyl group may be mentioned as examples.

The following may be mentioned as examples of acids for the preparation of the salts: sulphuric acid, hydrochloric acid, organic carboxylic acids, such as malic acid, citric acid, fumaric acid, maleic acid, succinic acid or acetic acid, and organic sulphonic acids, such as naphthalene-1,5-disulphonic acid.

The salts of the compounds of the formula (I) can be obtained in a simple manner by customary salt formation methods, for example by dissolving the base and adding the acid, and can be isolated in a known manner, for example by filtration, and, if required, purified.

In formula (I): $R_1$ and $R_2$ are identical or different and preferably represent hydrogen, $C_1$–$C_6$-alkyl, $C_5$–$C_7$-cycloalkyl, phenyl, optionally substituted (disubstituted, or in particular monosubstituted) by $C_1$–$C_4$-alkyl, halogen (chlorine or bromine) and/or $C_1$–$C_4$-alkoxy, or $C_7$–$C_9$-aralkyl, the aryl radical of which is optionally substituted (monosubstituted or disubstituted, in particular monosubstituted) by $C_1$–$C_4$-alkyl, halogen (chlorine or bromine) and/or $C_1$–$C_4$-alkoxy, or $R_1$ and $R_2$ together with the included C atom of the chroman ring, form a 4- to 7-membered carbocyclic ring; $R_3$ to $R_6$ are identical or different and preferably represent hydrogen, hydroxyl, halogen (chlorine or bromine), $C_1$–$C_6$-alkyl, $C_5$–$C_7$-cycloalkyl, phenyl, optionally substituted (monosubstituted or disubstituted, in particular monosubstituted) by $C_1$–$C_4$-alkyl, halogen (chlorine or bromine) and/or $C_1$–$C_4$-alkoxy, or $C_7$–$C_9$-aralkyl, the aryl radical of which is optionally substituted (monosubstituted or disubstituted, in particular monosubstituted) by $C_1$–$C_4$-alkyl, halogen (chlorine or bromine) and/or $C_1$–$C_4$-alkoxy; $R_7$, $R_8$, $R_9$, $R_{10}$ and $R_{11}$ are identical or different and represent hydrogen or $C_1$–$C_6$-alkyl, X represents a single bond or methylene which is optionally monosubstituted or disubstituted by $C_1$–$C_4$-alkyl, or represents oxygen or —$NR_{17}$, wherein $R_{17}$ represents hydrogen or $C_1$–$C_4$ alkyl, or $R_{17}$ together with $R_7$ forms a $C_2$-alkylene bridge $R_{12}$, $R_{13}$, $R_{14}$, $R_{15}$ and $R_{16}$ are identical or different and each represent hydrogen, hydroxyl, chlorine, fluorine, alkyl having 1–4C atoms, alkoxy having 1 to 3C atoms, aralkoxy having up to 8C atoms or trifluoromethyl, and at least one and at most two of these substituents $R_{12}$–$R_{16}$ are identical or different and each represents nitro, cyano or the

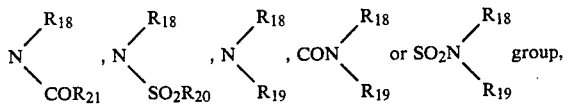

wherein $R_{18}$ and $R_{19}$ are identical or different and each represent hydrogen or alkyl having 1–4C atoms which is optionally monosubstituted to trisubstituted by halogen, $R_{20}$ represents alkyl having 1–6C atoms which is optionally monosubstituted or trisubstituted by halogen, $R_{21}$ represents hydrogen, alkyl, alkoxy or alkylamino, each having 1–4C atoms per alkyl and alkoxy group, the alkyl radical being optionally monosubstituted to trisubstituted by halogen, and $R_{12}$ and $R_{13}$ or $R_{13}$ and $R_{14}$ together optionally represent an alkylenedioxy group having 1 or 2C atoms or the group —CH=CH—CH=CH—, or wherein $R_{18}$ together with $R_{19}$ or together with $R_{20}$ or together with $R_{21}$ can form a 5-membered or 6-membered heterocyclic ring which contains an alkylene bridge having 2, 3 or 4 carbon atoms and which optionally also contains an additional carbonyl group.

Particularly preferred compounds of the formula (I) are those in which $R_1$ and $R_2$ are identical or different and represent hydrogen or $C_1$–$C_4$-alkyl, or $R_1$ and $R_2$, together with the carbon atom between them, form a carbocyclic $C_5$ or $C_6$ ring, $R_3$ to $R_6$ are identical or different and denote hydrogen, hydroxyl, $C_1$–$C_4$-alkyl, $C_1$–$C_4$-alkoxy or chlorine, $R_7$ to $R_{11}$ are identical or different and represent hydrogen or $C_1$–$C_4$-alkyl, X is a single bond, oxygen, methylene or —$NR_{17}$, wherein $R_{17}$ denotes hydrogen or $C_1$–$C_3$-alkyl, or wherein $R_{17}$ together with $R_7$ forms an ethylene group, and $R_{12}$ to $R_{16}$ are identical or different and denote hydrogen, chlorine, cyclohexyl, $C_1$–$C_4$-alkyl, $C_1$–$C_3$-alkoxy, aralkoxy having 1–8C atoms or trifluoromethyl, and $R_{12}$ and $R_{13}$ or $R_{13}$ and $R_{14}$ together optionally each form a methylenedioxy group or a —CH=CH—CH=CH— group, and wherein at least one and at most two substituents from the group comprising $R_{12}$–$R_{16}$ are identical or different and each represents nitro, cyano or the

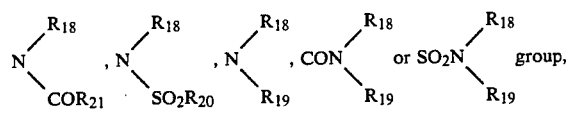

wherein $R_{18}$ and $R_{19}$ are identical or different and each represent hydrogen or alkyl having 1–4C atoms which is optionally substituted by fluorine or chlorine, and wherein $R_{20}$ represents alkyl having 1–4C atoms which is optionally substituted by fluorine or chlorine, and wherein $R_{21}$ represents hydrogen or alkyl having 1–4C atoms which is optionally substituted by fluorine or chlorine, or represents alkoxy or alkylamino, each having 1–2C atoms.

The following may be mentioned as examples of new compounds of the general formula (I): 4-{N-[4-(3-nitrophenyl)-2-butyl]-aminomethyl}-chroman, 4-{N-[4-(2-chloro-4-nitrophenyl)-2-butyl]-aminomethyl}-2,2-dimethyl-chromene, 4-{N-[4-(3,4-methylenedioxy-5-nitrophenyl)-2-butyl]-aminomethyl}-7-hydroxy-2,2-diisopropylchroman, 4-{N-[4-(4-methyl-5-nitrophenyl)-2-butyl]-aminomethyl}-2-spirocyclohexachroman, 4-{N-[4-(3-trifluoromethyl-5-nitrophenyl)-2-butyl]-aminomethyl}-6,7-dimethyl-2-spirocyclopentachroman, 4-{N-[4-(3,5-dinitrophenyl)-2-butyl]-aminomethyl}-7-chloro-2-benzylchromene, 4-{N-[4-(3-methoxy-4-hydroxy-5-nitrophenyl)-2-butyl]-aminomethyl}-5-methoxy-2-spirocyclopentachroman, 4-{N-[4-(3-N-methylaminophenyl)-2-butyl]-aminomethyl}-2-spirocyclopentachroman, 4-{N-[4-(3-methoxy-4-aminophenyl)-2-butyl]-aminomethyl}-2-spirocyclopentachroman, 4-{N-[4-(3-pyrrolidinophenyl)-2-butyl]-aminomethyl}-2-spirocyclopentachroman, 4-{N-[4-(3-methylsulphonylaminophenyl)-2-butyl]-aminomethyl}-chroman, 4-{N-[4-(2-chloro-4-methylsulphonylaminophenyl)-2-butyl]-aminomethyl}-2,2-dimethylchromene, 4-{N-[4-(3,4-methylenedioxy-5-methylsulphonylaminophenyl)-2-butyl]-aminomethyl}-7-hydroxy-2,2-diisopropylchroman, 4-{N-[4-(4-methyl-5-methylsulphonylaminophenyl)-2-butyl]-aminomethyl}-2-spirocyclohexachroman, 4-{N-[4-(3-trifluoromethyl-5-methylsulphonylaminophenyl)-2-butyl]-aminomethyl}-6,7-dimethyl-2-spirocyclopentachromene, 4-{[4-(3,5-bis-methylsulphonylamino-phenyl)-2-butyl]-aminomethyl}-6-chloro-2-benzylchromene, 4-{[4-(3-methoxy-4-hydroxy-5-methylsulphonylaminophenyl)-2-butyl]-aminomethyl}-2-spirocyclopentachroman, 4-{N-[4-(3-acetylaminophenyl)-2-butyl]-aminomethyl}-chroman, 4-{N-[4-(2-chloro-4-acetylaminophenyl)-2-butyl]-aminomethyl}-2,2-dimethylchromene, 4-{N-[4-(3,4-methylenedioxy-5-acetylaminophenyl)-2-butyl]-aminomethyl}-7-hydroxy-2,2-diisopropylchroman, 4-{N-[4-(4-methyl-5-acetylaminophenyl)-2-butyl]-aminomethyl}-2-spirocyclohexachroman, 4-{N-[4-(3-trifluoromethyl-5-acetylaminophenyl)-2-butyl]-aminomethyl}-6,7-dimethyl-2-spirocyclopentachromene, 4-{N-[4-(3,5-dinitrophenyl)-2-butyl]-aminomethyl}-7-chloro-2-benzylchromene, 4-{N-[4-(3-methoxy-4-hydroxy-5-acetylaminophenyl)-2-butyl]-aminomethyl}-5-methoxy-2-spirocyclopentachroman, 4-{N-[4-(4-cyanophenyl)-2-butyl]-aminomethyl}-2-spirocyclopentachroman, 4-{N-[4-(4-methyl-5-cyanophenyl)-2-butyl]-aminomethyl}-2-spirocyclopentachroman, 4-{N-[4-(4-methoxy-5-cyanophenyl)-2-butyl]-aminomethyl}-2-spirocyclopentachroman, 4-{N-[1-(3-methoxy-4-methylsulphonylamino-phenoxy)-2-propyl]-aminomethyl}-2-spirocyclopentachromene, 4-{N-[1-(3-aminophenoxy)-2-propyl]-aminomethyl}-2,2-dimethylchromene, 4-{N-[1-(3-N-methyl-methylsulphonylaminophenyl)-2-propyl]-aminomethyl}-7-chloro-2-spirocyclohexachroman, 4-{N-[1-(3-N-acetylaminophenoxy)-2-propyl]-6,7-dimethyl}-2-spirocyclopentachroman, 4-{N-[1-(2-methoxy-4-hydroxyphenyl)-2-methyl-isopropyl]-aminomethyl}-2-spirocyclopentachroman, 4-{N-[1-(3,4,5-trimethoxyphenyl)-2-methylisopropyl]-aminomethyl}-2-spirocyclopentachroman, 4-{N-[1-(2,6-dichloro-4-methoxyphenyl)-2-methyl-isopropyl]-aminomethyl}-2-spirocyclopentachroman, 4-{N-[1-(3,5-dichloro-4-methoxyphenyl)-2-methyl-isopropyl]-aminomethyl}-2-spirocyclopentachroman and 4-{N-[1-(2-chloro-4-hydroxyphenyl)-2-methyl-isopropyl]-aminomethyl}-2-spirocyclopentachroman.

The invention furthermore relates to various processes for the preparation of the compounds of the formula (I).

Either (A) chroman-4-carbaldehydes of the formula (II)

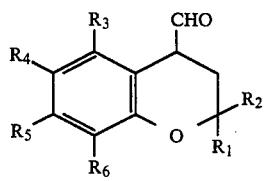

in which $R_1$, $R_2$, $R_3$, $R_4$, $R_5$ and $R_6$ have the meaning given above, are reacted with amines of the formula (III)

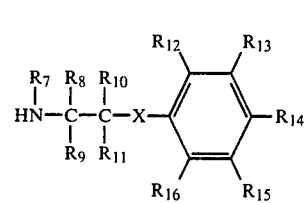

in which $R_7$, $R_8$, $R_9$, $R_{10}$, $R_{11}$, $R_{12}$, $R_{13}$, $R_{14}$, $R_{15}$, $R_{16}$, $R_{17}$ and X have the meaning given above, in the presence of reducing agents, or (B) amines of the formula (IV)

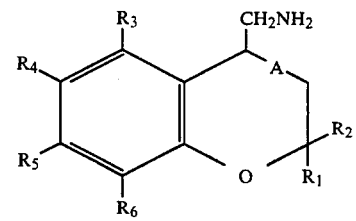

in which A, $R_1$, $R_2$, $R_3$, $R_4$, $R_5$ and $R_6$ have the meaning given above, are reacted with carbonyl compounds of the formula (V)

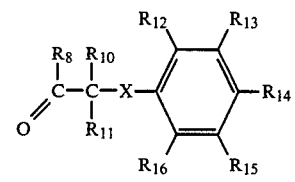

in which $R_8$ to $R_{16}$ have the meaning given above, with the proviso that X does not represent $NR_{17}$, in the presence of reducing agents, or (C) compounds of the formula (VI)

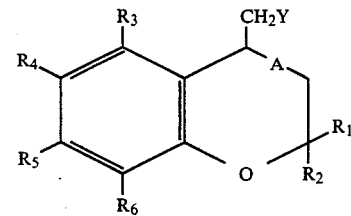

in which

A, $R_1$, $R_2$, $R_3$, $R_4$, $R_5$ and $R_6$ have the meaning given above, and Y represents a nucleophilically displaceable group, such as alkyl-substituted or aryl-substituted sulphonyloxy groups, bromine or chlorine, are reacted with the amines of the formula (III) in the presence of an acid-binding agent.

Complex metal hydrides may be mentioned as examples of reducing agents which can be employed in process variants A and B. Alkali metal borohydrides, alkali metal cyanoborohydrides and/or alkali metal alanates, in particular sodium compounds or lithium compounds, are preferred. Sodium borohydride, sodium cyanoborohydride and lithium alanate may be mentioned specifically. It is also possible to use catalytically activated hydrogen at elevated pressures and temperatures.

The reducing agents can be employed in from equivalent amounts to an excess of 100%, preferably from equivalent amounts to an excess of 20%, relative to the carbonyl compound used.

The acid-binding agents employed in preparation variant C are known bases. The following may be mentioned as examples: alkaline earth metal or alkali metal hydroxide, such as sodium hydroxide and/or potassium hydroxide, alkaline earth metal and alkali metal carbonates, such as sodium bicarbonate or potassium carbonate, and organic nitrogen bases, such as triethylamine, tributylamine or benzyltrimethylammonium hydroxide.

These acid-binding agents can be employed in from equivalent amounts to an excess of 100%, preferably from equivalent amounts to an excess of 20%, relative to the halogen compound used.

The reactions according to the invention are carried out in solvents. Suitable solvents are all solvents which are inert for the particular reaction, the following being preferably mentioned: alcohols, such as methanol, ethanol, isopropanol or tert.-butanol, ethers, such as diethyl ether, diisopropyl ether, tetrahydrofuran or dioxane, hydrocarbons, such as hexane, cyclohexane, benzene or toluene, chlorohydrocarbons, such as methylene chloride, chloroform, carbon tetrachloride or chlorobenzene, and furthermore acetonitrile, dimethylformamide, dimethyl sulphoxide or mixtures of such solvents.

The reaction temperatures can be varied within a relatively wide range. In general, the reaction is carried out at between $-50°$ and $150°$ C., preferably from $-10°$ to $120°$ C.

In carrying out the process according to the invention, 0.5 to 2 mols of the amine of the formula (III) or of the carbonyl compound of the formula (V) are preferably reacted per mol of the chroman or chromene compound.

The molar ratio of the reactants is particularly preferably 1:1. If an excess is used, it is preferable to employ an excess of the amine of the formula (III) or of the carbonyl compound of the formula (V).

The reaction products can be obtained by distillation, crystallization, evaporation and recrystallization, or chromatographic separation.

The preparation of the chroman-4-aldehydes of the formula (II) is carried out by hydroformylation of 2H-chromenes, according to the following equation:

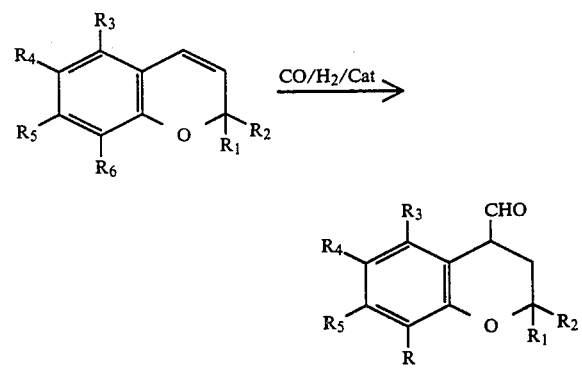

The process is characterized in that the 2H-chromenes are reacted with carbon monoxide and hydrogen in the presence of metal catalysts from sub-group 8 of the periodic table, at temperatures of 80° to 250° C. and pressures of 20–1,000 bar.

The following may be mentioned as examples of the chroman-4-carbaldehydes (II): 4-formylchroman, 4-formyl-2-methylchroman, 4-formyl-2,2-dimethylchroman, 4-formyl-2-propylchroman, 4-formyl-2-isopropylchroman, 4-formyl-2,2-diethylchroman, 4-formyl-2-methyl-2-propylchroman, 4-formyl-2-hexylchroman, 4-formyl-2-cyclopentylchroman, 4-formyl-2-cyclohexylchroman, 4-formyl-2-spirocyclopentachroman, 4-formyl-2-spirocyclohexachroman, 4-formyl-6-methyl-2-spirocyclopentachroman, 4-formyl-7-methyl-2-spirocyclopentachroman, 4-formyl-6,8-dimethyl-2-spirocyclopentachroman, 4-formyl-6-chloro-2-spirocyclopentachroman, 4-formyl-6-methoxy-2-spirocyclopentachroman, 4-formyl-7-methoxy-2-spirocyclopentachroman, 4-formyl-7-isopropoxy-2-spirocyclopentachroman, 4-formyl-7-phenoxy-2-spirocyclopentachroman, 4-formyl-7-benzyloxy-2-spirocyclopentachroman, 4-formyl-7-phenyl-2-spirocyclopentachroman, 4-formyl-6-methyl-2,2-dimethylchroman, 4-formyl-6-chloro-2,2-dimethylchroman, 4-formyl-7-methoxy-2,2-dimethylchroman, 4-formyl-6-methyl-2-spirocyclohexachroman and 4-formyl-7-methoxy-2-spirocyclohexachroman.

Some of the amines of the formula (III) which are employed in the preparation of the compounds according to the invention are known (see, for example, Arch. Pharm. 316, 193 (1983)), or can be obtained by analogous methods.

The following may be mentioned as examples of the amines of the formula (III): 1-(4-hydroxyphenyl)-2-methyl-isopropylamine, 1-(2-methoxy-4-hydroxyphenyl)-2-methyl-isopropylamine, 1-(2,6-dimethyl-4-hydroxyphenyl)-2-methyl-isopropylamine, 1-(2-chloro-4-hydroxyphenyl)-2-methyl-isopropylamine, 1-(3,5-dimethyl-4-methoxyphenyl)-2-methyl-isopropylamine, 1-(3,4,5-trimethoxyphenyl)-2-methyl-isopropylamine, 1-(2,6-dichloro-4-methoxyphenyl)-2-methyl-isopropylamine, 1-(3,5-dichloro-4-methoxy-phenyl)-2-methyl-isopropylamine, 2-amino-4-(3-nitrophenyl)-butane, 2-amino-4-(3-methylsulphonylaminophenyl)-butane, 2-amino-4-(4-methylsulphonylaminophenyl)-butane, 2-amino-4-(3-acetaminophenyl)-butane, 2-amino-4-(2-nitrophenyl)-butane, 2-amino-4-(3-N,N-dimethylaminosulphonylphenyl)-butane, 2-amino-4-(3-N-methylcarbamoylphenyl)-butane and 2-amino-4-(3,4-dimethoxy-5-methylsulphonylaminophenyl)-butane.

Some of the amines of the formula (IV) which are employed for the preparation of the compounds according to the invention are known (J. med. Chem. 1982, 393), or can be prepared by analogous procedures.

For example, the following process routes are represented by equations, starting from chroman-4-ones:

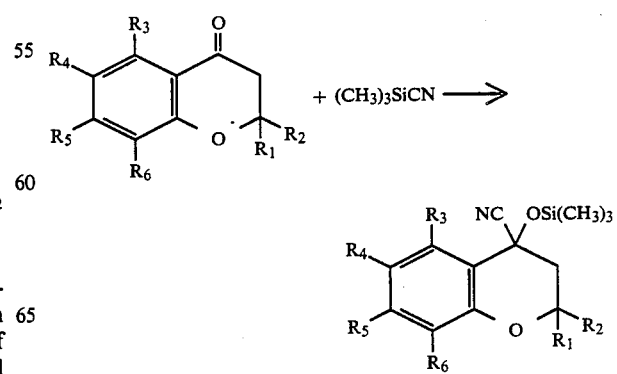

The 4-cyano-4trimethylsilyloxychromans formed in this reaction can be hydrogenated with lithium aluminum hydride to give 4-aminomethyl-4-hydroxychromans, as shown in the following equation:

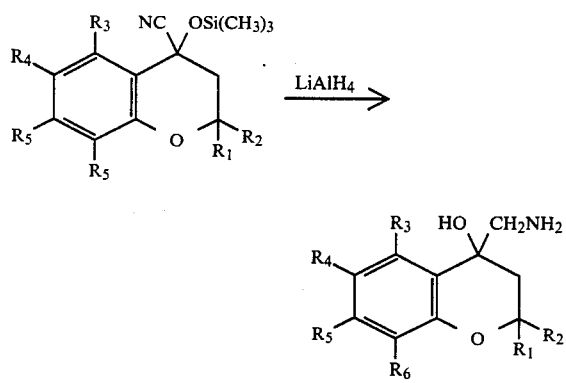

The 4-aminomethyl-4-hydroxy-chromans can be converted to the 4-aminomethyl-2H-chromenes of the formula (IV) by means of agents which eliminates water, as shown in the equation below.

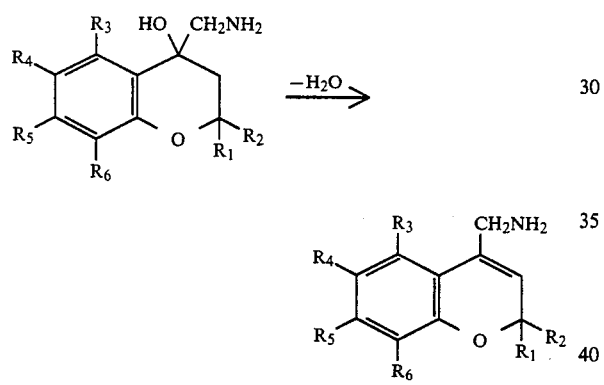

The aminomethylchromans can be obtained from the aminomethylchromenes by hydrogenation, as in the equation below:

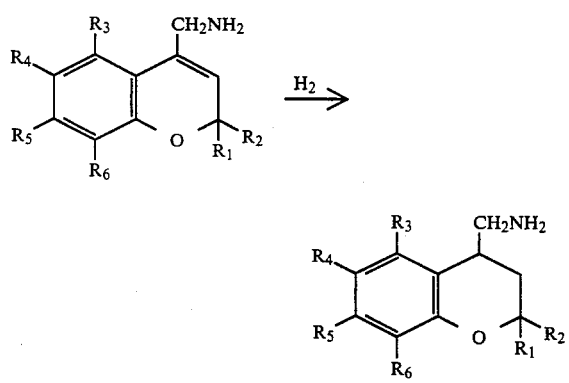

However, it is also possible to eliminate trimethylsilanol from the 4-cyano-4-trimethylsilyloxychromans with the aid of phosphorus oxychloride/pyridine, and thus to obtain 4-cyano-2H-chromenes, as shown in the equation below (analogously to a procedure from Chemistry Letters 1979, 1427):

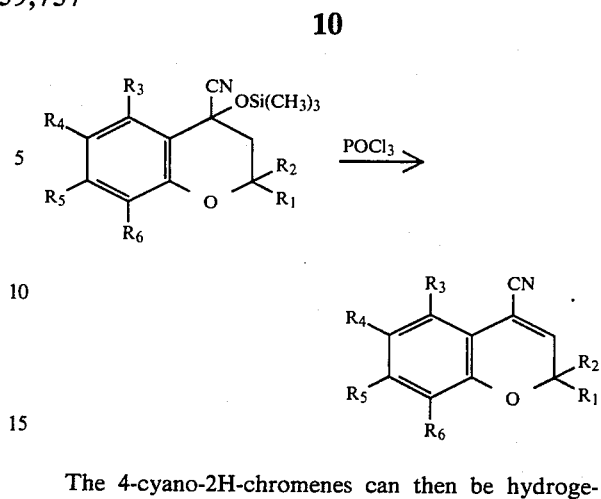

The 4-cyano-2H-chromenes can then be hydrogenated via the 4-cyanochromans, either directly or in stages, to give the 4-aminomethylchromans of the formula (IV), as represented in the equation below:

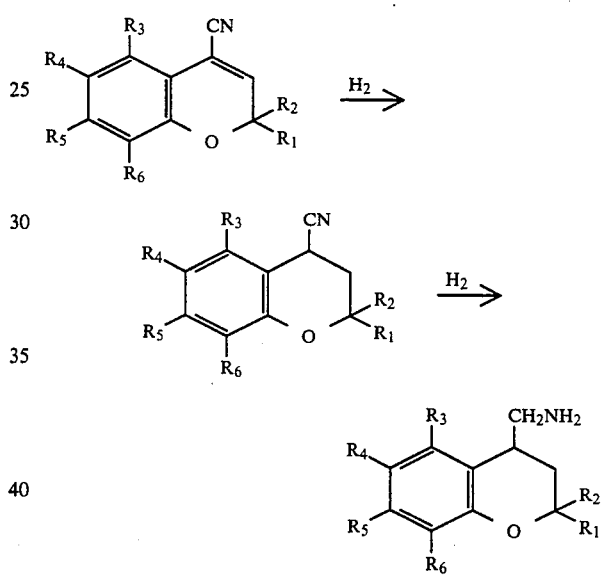

The following may be mentioned as examples of the 4-aminomethyl-2H-chromenes (IV): 4-aminomethyl-2H-chromene, 4-aminomethyl-2-methyl-2H-chromene, 4-aminomethyl-2,2-dimethyl-chromene, 4-aminomethyl-2-propyl-2H-chromene, 4-aminomethyl-2-isopropyl-2H-chromene, 4-aminomethyl-2,2-diethyl-chromene, 4-aminomethyl-2-methyl-2-propyl-chromene, 4-aminomethyl-2-hexyl-2H-chromene, 4-aminomethyl-2-cyclopentyl-2H-chromene, 4-aminomethyl-2-cyclohexyl-2H-chromene, 4-aminomethyl-2-spirocyclopentachromene, 4-aminomethyl-2-spirocyclohexachromene, 4-aminomethyl-6-methyl-2-spirocyclopentachromene, 4-aminomethyl-7-methyl-2-spirocyclopentachromene, 4-aminomethyl-6,8-dimethyl-2-spirocyclopentachromene, 4-aminomethyl-6-chloro-2-spirocyclopentachromene, 4-aminomethyl-6-methoxy-2-spirocyclopentachromene, 4-aminomethyl-7-methoxy-2-spirocyclopentachromene, 4-aminomethyl-7-isopropoxy-2-spirocyclopentachromene, 4-aminomethyl-7-phenoxy-2-spirocyclopentachromene, 4-aminomethyl-7-benzyloxy-2-spirocyclopentachromene, 4-aminomethyl-7-phenyl-2-spirocyclopentachromene, 4-aminomethyl-6-methyl-2-spirocyclohexachromene, 4-aminomethyl-6-chloro-2-spirocyclohexachromene, 4-aminomethyl-7- methoxy-2-spirocyclohexachromene, 4-aminomethyl-6-methyl-2,2-dimethylchromene and 4-aminomethyl-7-methoxy-2,2-dimethylchromene.

Some of the amines of the formula (IV) which are employed in the preparation of the compounds according to the invention are known (J. med. Chem. 1982, 393), or can be obtained by analogous procedures, for example as described above.

The following may be mentioned as examples of the 4-aminomethylchromans (IV): 4-aminomethyl-chroman, 4-aminomethyl-2-methyl-chroman, 4-aminomethyl-2,2-dimethylchroman, 4-aminomethyl-2-propyl-chroman, 4-aminomethyl-2-isopropyl-chroman, 4-aminomethyl-2,2-diethyl-chroman, 4-aminomethyl-2-methyl-2-propyl-chroman, 4-aminomethyl-2-hexyl-chroman, 4-aminomethyl-2-cyclopentyl-chroman, 4-aminomethyl-2-cyclohexyl-chroman, 4-aminomethyl-2-spirocyclopenta-chroman, 4-aminomethyl-2-spirocyclohexa-chroman, 4-aminomethyl-6-methyl-2-spirocyclopenta-chroman, 4-aminomethyl-7-methyl-2-spirocyclopenta-chroman, 4-aminomethyl-6,8-dimethyl-2-spirocyclopenta-chroman, 4-aminomethyl-6-chloro-2-spirocyclopenta-chroman, 4-aminomethyl-6-methoxy-2-spirocyclopenta-chroman, 4-aminomethyl-7-methoxy-2-spirocyclopenta-chroman, 4-aminomethyl-8-isopropoxy-2-spirocyclopenta-chroman, 4-aminomethyl-7-phenoxy-2-spirocyclopenta-chroman, 4-aminomethyl-7-benzyloxy-2-spirocyclopenta-chroman, 4-aminomethyl-7-phenyl-2-spirocyclopenta-chroman, 4-aminomethyl-6-methyl-2-spirocyclohexachroman, 4-aminomethyl-6-chloro-2-spirocyclohexachroman, 4-aminomethyl-7-methoxy-2-spirocyclohexachroman, 4-aminomethyl-6-methyl-2,2-dimethylchroman and 4-aminomethyl-7-methoxy-2,2-dimethylchroman.

The carbonyl compounds of the formula (V) which are used in the preparation according to the invention are known (see, for example, Beilsteins Handbuch der organischen Chemie (Beilstein's Handbook of Organic Chemistry) 6, 151, II 152; 7, 292, 303, 304, 314, I 154, 161, 162, 167, II 226, 233, 236, 243), or can be prepared by analogous methods.

The following may be mentioned as examples of the carbonyl compounds (V): 4-(3-carbamoylphenyl)-butan-2-one; 4-(4-carbamoylphenyl)-butan-2-one; 4-(2-carbamoylphenyl)-butan-2-one; 4-(2-chloro-5-carbamoylphenyl)-butan-2-one; 4-(4,5-dimethoxy-3-carbamoylphenyl)-butan-2-one; 4-(3-methoxy-5-carbamoylphenyl)-butan-2-one; 4-(3-methyl-5-carbamoylphenyl)-butan-2-one; 4-(3-trifluoromethyl-5-carbamoylphenyl)-butan-2-one; 4-(3-methoxy-4-hydroxy-5-carbamoylphenyl)-butan-2-one; 4-(4-methoxy-5-carbamoylphenyl)-butan-2-one; 4-(2-methyl-4-carbamoylphenyl)-butan-2-one; 4-(2,4-dichloro-5-carbamoylphenyl)-butan-2-one; 4-(3,4-methylenedioxy-5-carbamoylphenyl)-butan-2-one; 4-(3-aminosulphonylphenyl)-butan-2-one; 4-(4-aminosulphonylphenyl)-butan-2-one; 4-(2-aminosulphonylphenyl)-butan-2-one; 4-(2-chloro-5-aminosulphonylphenyl)-butan-2-one; 4-(4,5-dimethoxy-3-aminosulphonylphenyl)-butan-2-one; 4-(3-methoxy-5-aminosulphonylphenyl)-butan-2-one; 4-(3-methyl-5-aminosulphonylphenyl)-butan-2-one; 4-(3-trifluoromethyl-5-aminosulphonylphenyl)-butan-2-one; 4-(3-methoxy-4-hydroxy-5-aminosulphonylphenyl)-butan-2-one; 4-(3-chloro-5-aminosulphonylphenyl)-butan-2-one; 4-(4-methoxy-5-aminosulphonylphenyl)-butan-2-one; 4-(2-methyl-4-aminosulphonylphenyl)-butan-2-one; 4-(2,4-dichloro-5-aminosulphonylphenyl)-butan-2-one; 4-(3,4-methylenedioxy-5-aminosulphonylphenyl)-butan-2-one; 4-(3-aminophenyl)-butan-2-one; 4-(3-N-methylaminophenyl)-butan-2-one; 4-(3-N,N-dimethylaminophenyl)-butan-2-one; 4-(3-N-succinimidophenyl)-butan-2-one; 4-(3-ethylsulphonylaminophenyl)-butan-2-one; 4-(3-n-butylsulphonylaminophenyl)-butan-2-one; 4-(3-N-methylmethylsulphonylaminophenyl)-butan-2-one; 4-(3-propionylaminophenyl)-butan-2-one; 4-(3-N-methylacetylaminophenyl)-butan-2-one; 4-(4-cyanophenyl)-butan-2-one; 4-(4-methoxy-5-cyanophenyl)-butan-2-one; 4-(3-pyrrolidinophenyl)-butan-2-one; 1-(4-nitrophenoxy)-propan-2-one; 1-(3-nitrophenoxy)-propan-2-one; 1-(3-aminophenoxy)-propan-2-one; 1-(3-methylsulphonylaminophenoxy)-propan-2-one; 1-(4-N-methylmethylsulphonylaminophenoxy)-propan-2-one; 1-(3-N-acetylaminophenoxy)-propan-2-one; 1-(3-N,N-dimethylaminosulphonylphenoxy)-propan-2-one; 1-(4-aminosulphonylphenoxy)-propan-2-one; 1-(4-carbamoylphenoxy)-propan-2-one; 4-(3-nitrophenyl)-butan-2-one; 4-(4-nitrophenyl)-butan-2-one; 4-(2-nitrophenyl)-butan-2-one; 4-(2-chloro-4-nitrophenyl)-butan-2-one; 4-(4,5-dimethoxy-3-nitrophenyl)-butan-2-one; 4-(3-methoxy-5-nitrophenyl)-butan-2-one; 4-(3-methyl-5-nitrophenyl)-butan-2-one; 4-(3-trifluoromethyl-5-nitrophenyl)-butan-2-one; 4-(3,5-dinitrophenyl)-butan-2-one; 4-(3methoxy-4-hydroxy-5-nitrophenyl)-butan-2-one; 4-(3-chloro-5-nitrophenyl)-butan-2-one; 4-(4-methoxy-5-nitrophenyl)-butan-2-one; 4-(2-methyl-4-nitrophenyl)-butan-2-one; 4-(2,4-dichloro-5-nitrophenyl)-butan-2-one; 4-(3,4-methylenedioxy-5-nitrophenyl)-butan-2-one; 4-(3-methylsulphonylaminophenyl)-butan-2-one; 4-(4-methylsulphonylaminophenyl)-butan-2-one; 4-(2-methylsulphonylaminophenyl)-butan-2-one; 4-(2-chloro-5-methylsulphonylaminophenyl)-butan-2-one; 4-(4,5-dimethoxy-3-methylsulphonylaminophenyl)-butan-2-one; 4-(3-methoxy-5-methylsulphonylaminophenyl)-butan-2-one; 4-(3-methyl-5-methylsulphonylaminophenyl)-butan-2-one; 4-(3-trifluoromethyl-5-methylsulphonylaminophenyl)-butan-2-one; 4-(3,5-bis-methylsulphonylaminophenyl)-butan-2-one; 4-(3-methoxy-4-hydroxy-5-methylsulphonylaminophenyl)-butan-2-one; 4-(3-chloro-5-methylsulphonylaminophenyl)-butan-2-one; 4-(4-methoxy-5-methylsulphonylaminophenyl)-butan-2-one; 4-(2-methyl-4-methylsulphonylaminophenyl)-butan-2-one; 4-(2,4-dichloro-5-methylsulphonylaminophenyl)-butan-2-one; 4-(3,4-methylenedioxy-5-methylsulphonylaminophenyl)-butan-2-one; 4-(3-acetylaminophenyl)-butan-2-one; 4-(4-acetylaminophenyl)-butan-2-one; 4-(2-acetylaminophenyl)-butan-2-one; 4-(2-chloro-5-acetylaminophenyl)-butan-2-one; 4-(4,5-dimethoxy-3-acetylaminophenyl)-butan-2-one; 4-(3-methoxy-5-acetylaminophenyl)-butan-2-one; 4-(3-methyl-5-acetylaminophenyl)-butan-2-one; 4-(3-trifluoromethyl-5-acetylaminophenyl)-butan-2-one; 4-(3,5-bis-acetylaminophenyl)-butan-2-one; 4-(3-methoxy-4-hydroxy-5-acetylaminophenyl)-butan-2-one; 4-(3-chloro-5-acetylaminophenyl)-butan-2-one; 4-(4-methoxy-5-acetylaminophenyl)-butan-2-one; 4-(2-methyl-4-acetylaminophenyl)-butan-2-one; 4-(2,4-dichloro-5-acetylaminophenyl)-butan-2-one and 4-(3,4-methylenedioxy-5-acetylaminophenyl)-butan-2-one.

Some of the compounds of the formula (VI) which are employed for the preparation of the compounds according to the invention are known (Tetrahedron 23, 1893 (1967)), or can be obtained in an analogous manner or from 4-methyl-2H-chromenes [Heterocyclic Compounds, Vol. 31, ed. G. P. Ellis (New York 1977), page 11 et seq.] by halogenation with N-bromo- or N-chlorosuccinimide (Wohl-Ziegler reaction).

The following may be mentioned as examples of the compounds of the formula VI: 4-chloromethyl-2H-chromene, 4-bromomethyl-2-methyl-2H-chromene, 4-bromomethyl-2,2-dimethylchromene, 4-bromomethyl-2-isopropyl-2H-chromene, 4-chloromethyl-2,2-diethylchromene, 4-chloromethyl-2methyl-2-propyl-chromene, 4-bromomethyl-2-hexyl-2H-chromene, 4-bromomethyl-2-cyclopentyl-2H-chromene, 4-bromomethyl-2-cyclohexyl-2H-chromene, 4-bromomethyl-2-spiro-cyclopentachromene, 4-bromomethyl-2-spirocyclohexachromene, 4-bromomethyl-6-methyl-2-spirocyclopentachromene, 4-bromomethyl-7-methyl-2-spirocyclopentachromene, 4-bromomethyl-6,8-dimethyl-2-spirocyclopentachromene, 4-bromomethyl-3-chloro-2-spirocyclopentachromene, 4-bromomethyl-6-methoxy-2-spirocyclopentachromene, 4-bromomethyl-7-methoxy-2-spirocyclopentachromene, 4-bromomethyl-7-isopropoxy-2-spirocyclopentachromene, 4-bromomethyl-7-phenoxy-2-spirocyclopentachromene, 4-bromomethyl-7-benzyloxy-2-spirocyclopentachromene, 4-bromomethyl-7-phenyl-2-spirocyclopentachromene, 4-bromomethyl-6-methyl-2,2-dimethylchromene, 4-bromomethyl-6-chloro-2,2-dimethylchromene, 4-bromomethyl-7-methoxy-2,2-dimethylchromene, 4-bromomethyl-6-methyl-2-spirocyclohexachromene, 4-bromomethyl-7-methoxy-2-spirocyclohexachromene, 4-(p-tosyloxymethyl)-2-spirocyclopentachroman and 4-mesyloxymethyl-2-spirocyclopentachroman.

The chroman and chromene derivatives according to the invention surprisingly have an antihypertensive action and, in the free form or in the form of their pharmaceutically acceptable acid addition salts, can therefore be employed as medicaments.

The new compounds have a broad and varied pharmacological action spectrum and a surprisingly long duration of action.

Specifically, it has been possible to demonstrate the following principal actions in an animal experiment:

1. The tone of the smooth muscle of the vessels is greatly reduced under the action of the compounds. This vascular-spasmolytic action can take place in the entire vascular system or can manifest itself more or less isolated in circumscribed vascular regions. The compounds are therefore particularly suitable as cerebral therapeutic agents.

2. The compounds lower the blood pressure of normotonic and hypertonic animals and can thus be used as antihypertensive agents.

The compounds according to the invention are particularly suitable for the treatment of acute and chronic heart diseases, for the therapy of hypertension and for the treatment of cerebral and peripheral dysfunctions and cerebral and peripheral disturbances of blood flow.

The new active compounds can be converted in a known manner into the customary formulations, such as tablets, capsules, dragees, pills, granules, aerosols, syrups, emulsions, suspensions and solutions, using inert, non-toxic, pharmaceutically suitable excipients or solvents. The therapeutically active compound should in each case be present in a concentration of about 0.5 to 90% by weight of the total mixture, that is to say in amounts which suffice to achieve the indicated dosage range.

The formulations are prepared, for example, by extending the active compounds with solvents and/or excipients, using emulsifiers and/or dispersing agents if appropriate, and, for example in the case of water being employed as the diluent, organic solvents can be used as auxiliary solvents if appropriate.

As examples of auxiliary substances there may be mentioned: water, non-toxic organic solvents, such as paraffins (for example petroleum fractions), vegetable oils (for example groundnut oil/sesame oil), alcohols (for example ethyl alcohol and glycerol), glycols (for example propylene glycol and polyethylene glycol), solid excipients such as, for example, natural rock powders (for example kaolins, aluminas, talc and chalk), synthetic rock powders (for example highly disperse silica and silicates) and sugars (for example raw sugar, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl-sulphate).

Administration is effected in the customary manner, preferably orally or parenterally, especially perlingually or intravenously. In the case of oral use, tablets can of course also contain, in addition to the excipients mentioned, additives such as sodium citrate, calcium carbonate and dicalcium phosphate, together with various further substances such as starch, preferably potato starch, gelatine and the like. Furthermore, lubricants such as magnesium stearate, sodium lauryl-sulphate and talc can be used conjointly for tablet-making. In the case of aqueous suspensions and/or elixirs which are intended for oral use the active compounds can be mixed with various flavor-improving agents or dyestuffs in addition to the abovementioned auxiliaries.

In the case of parenteral application, solutions of the active compounds can be employed, using suitable liquid excipients.

In general it has proved advantageous, in the case of intravenous administration, to administer amounts of about 0.001 to 1 mg/kg, preferably about 0.01 to 0.5 mg/kg of body weight daily to achieve effective results, whilst in the case of oral administration the dosage is about 0.5 to 20 mg/kg, preferably 0.1 to 10 mg/kg of body weight daily.

Nevertheless it can at times be necessary to deviate from the amounts mentioned and in particular to do so as a function of the body weight of the test animal or of the nature of the administration route, but also because of the type of animal and its individual behaviour towards the medicine or the nature of its formulation and the time or interval at which it is administered. Thus it may suffice, in some cases, to manage with less than the abovementioned minimum amount while in other cases the upper limit mentioned must be exceeded. Where major amounts are administered it can be advisable to divide these into several administrations over the course of the day. The same dosage range is envisaged for administration in human medicine. Here, again, the general sense of the above comments applies.

EXAMPLES ACCORDING TO THE INVENTION

Preparation according to process variant A

EXAMPLE 1

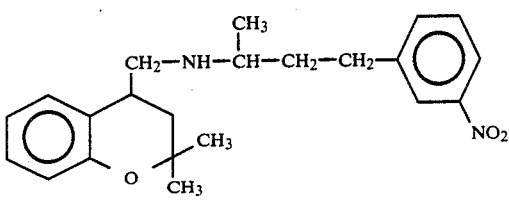

12.1 g (0.1 mol) of 2-amino-4-(3-nitrophenyl)butane are added to 19.0 g (0.1 mol) of 2,2-dimethyl-4-formyl-chroman in 100 ml of methanol at 20° C., with stirring and slight cooling, and the mixture is stirred for 1.5 hours. Thereafter, 4.5 g of sodium boranate are added, and stirring is continued for 1 day, and the mixture is evaporated down and worked up with ethyl acetate/water. The ethyl acetate phase is washed with water, dried and evaporated down. Distillation gives 4-{N-[4-(3-nitrophenyl)-2-butyl]-aminomethyl}-2,2-dimethyl-chroman. B.p.: 225°–235° C./0.04 mmHg.

EXAMPLE 2

(Preparation according to process variant B)

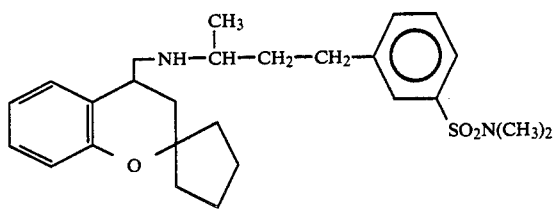

A solution of 6.5 g of 2,2-spirocyclopentane-4-aminomethylchroman, 9 g of 4-(m-dimethylaminosulphonylphenyl)-butan-2-one and 50 ml of toluene is heated in a water separator for 2 hours, after which it is evaporated down. The residue is stirred in 150 ml of methanol, and 5 g of sodium boranate are added at <25° C. After 2 days, the mixture is evaporated down, the residue is partitioned between water and toluene, and the toluene phase is evaporated down. The residue (14.5 g) is dissolved in ether, and a solution of 3 g of maleic acid in 35 ml of tetrahydrofuran is added. The precipiate formed is filtered off under suction after 1 day and is dried, and 11.5 g of the maleic acid salt of 2,2-spirocyclopentane-4-[N-(4-m-dimethylaminosulphonylphenyl)-2-butyl]-aminomethylchroman are formed, this salt melting at 113°–120° C.

EXAMPLE 3

(Preparation according to process variant B)

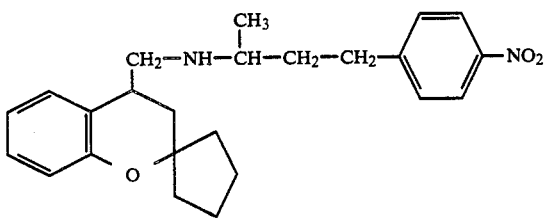

21.73 g (0.1 mol) of 2-spirocyclopenta-4-aminomethylchroman are boiled with 19.3 g (0.1 mol) of 4-(4-nitrophenyl)-butan-2-one in 150 ml of toluene until separation of water is complete. The mixture is evaporated down, the residue is taken up in 100 ml of absolute methanol, and 3.78 g (0.1 mol) of sodium borohydride are added in portions. After 2 hours at room temperature, the mixture is evaporated down, the residue is partitioned between 50 ml of CH₂Cl₂ and 50 ml of water, and the organic phase is washed once with 2N NaOH, dried over Na₂SO₄ and once again evaporated down. The residue is distilled in a bulb tube in a high vacuum, or chromatographed over silica gel with 2:1 CH₂Cl₂/acetone. B.p.: 250° C./0.3 mm Hg Yield: 24.63 g (63% of theory).

EXAMPLE 4

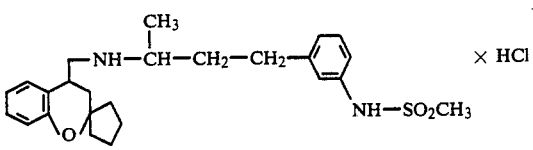

21.73 g (0.1 mol) of 2-spirocyclopenta-4-aminomethylchroman are reacted with 24 g (0.1 mol) of 4-(3-methylsulphonylaminophenyl)-butan-2-one as in Example 3. The residue is chromatographed rapidly over silica gel with CH₂Cl₂/acetone in a ratio of 2:1, the product-containing fractions are evaporated down, and the residue is partitioned between CH₂Cl₂ and 10% HCl. After standing overnight, the hydrochloride precipitated between the two phases is filtered off, rinsed with ether and dried. Yield 28.3 g (59% of theory), m.p.: 218°–231° C. (hydrochloride).

EXAMPLE 5

(Preparation according to process variant C)

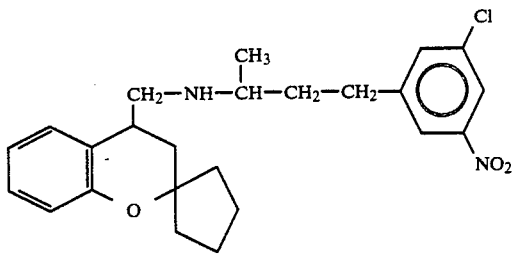

3 g (15.2 mmol) of 2-spirocyclopenta-4-p-tosyloxymethylchroman are refluxed for 10 hours together with 2.94 g (15.2 mmol) of 4-(3-chloro-5-nitrophenyl)-2-aminobutane and 2.1 g (15.2 mmol) of K₂CO₃ in 30 ml of acetonitrile. The mixture is evaporated down, the residue is taken up in 60 ml of CH₂Cl₂ and the solution is washed once with 60 ml of 2N HCl, once with 60 ml of 2N NaOH and once with 60 ml of H₂O. The solution is dried over Na₂SO₄, after which it is evaporated down, and the residue is distilled at 200°–210° C./0.1 mm Hg.

Yield: 3.05 g (51%).

The analogous reaction of 10.86 g of 2-spirocyclopenta-4-aminomethylchroman with 13.61 g of 4-(3,4-methylenedioxyphenyl)-butan-2-ol mesylate gives 5.91 g (30.1% of theory) of product.

The following compounds were obtained in an analogous manner, by process variant B:

EXAMPLE 6
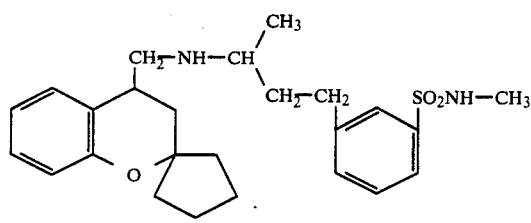
Oil;
EXAMPLE 7
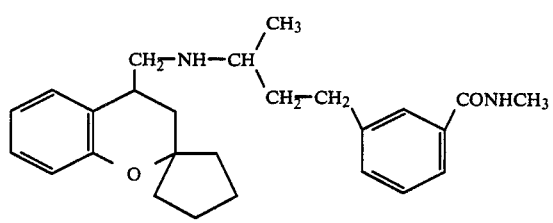
Oil; b.p.: 270° C./0.01 mm Hg
EXAMPLE 8
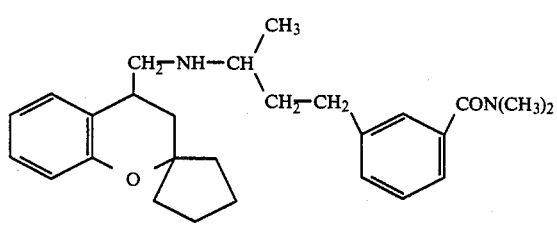
Oil; b.p.: 260°–270° C./0.01 mm Hg
EXAMPLE 9
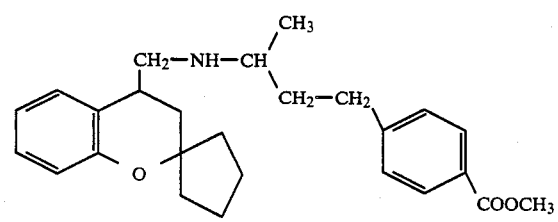
Oil; b.p.: 240°–250° C./0.02 mm Hg
EXAMPLE 10
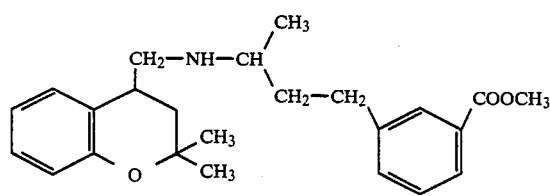
Oil; b.p.: 220°–240° C./0.01 mm Hg
EXAMPLE 11
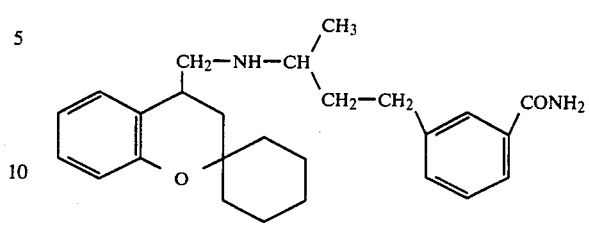
Oil; b.p.: 270°–280° C./0.01 mmHg
EXAMPLE 12
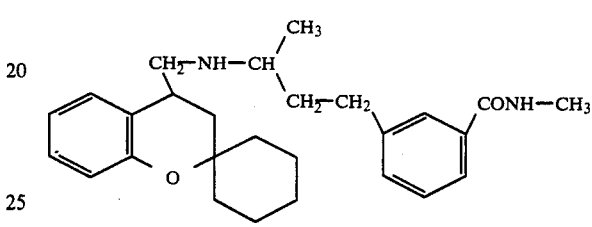
Oil; b.p.: 260°–270° C./0.02 mmHg
EXAMPLE 13
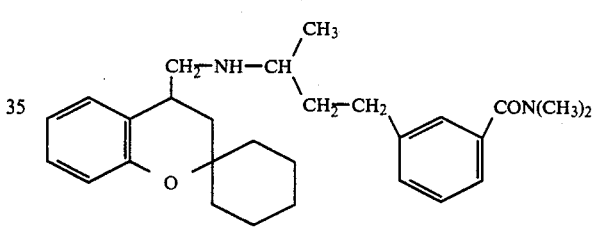
Oil; b.p.: 260° C./0.01 mmHg
EXAMPLE 14
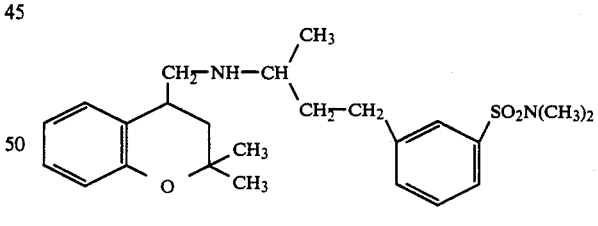
Oil;
EXAMPLE 15
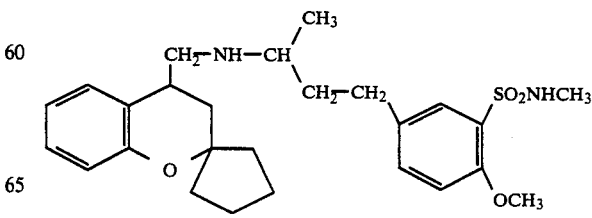
Oil;

EXAMPLE 16
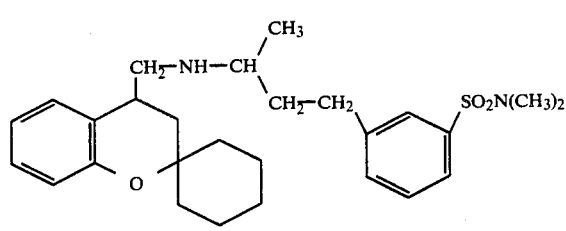
Oil;
EXAMPLE 17
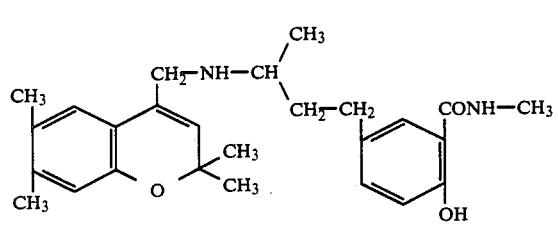
Oil;
EXAMPLE 18
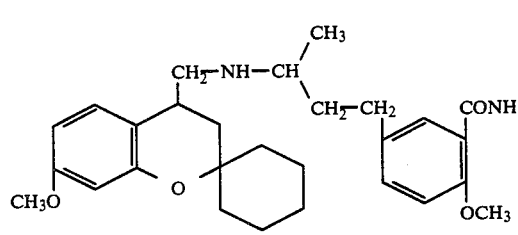
Oil;
EXAMPLE 19
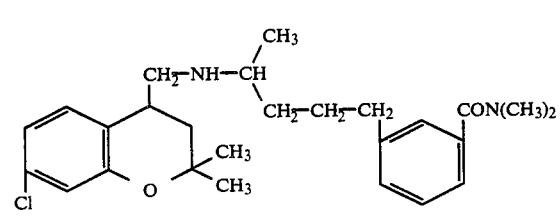
Oil;
EXAMPLE 20
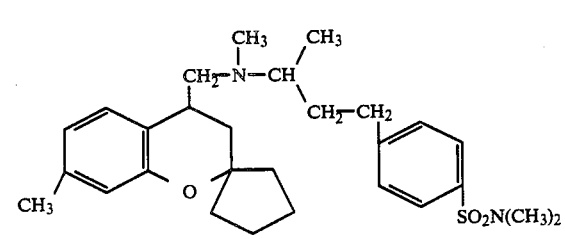
Oil;
EXAMPLE 21
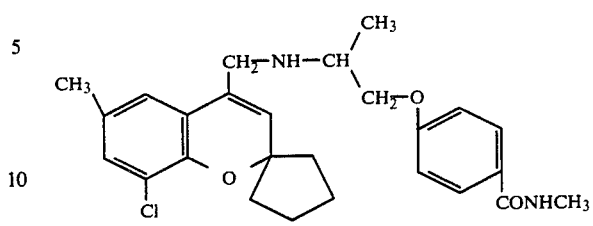
Oil;
EXAMPLE 22
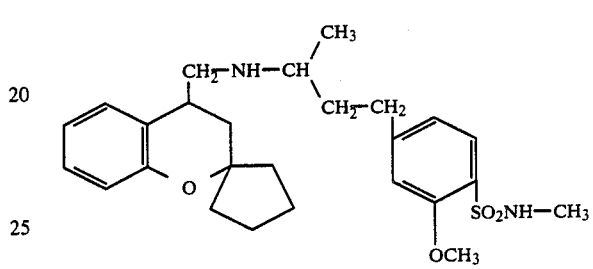
Oil;
EXAMPLE 23
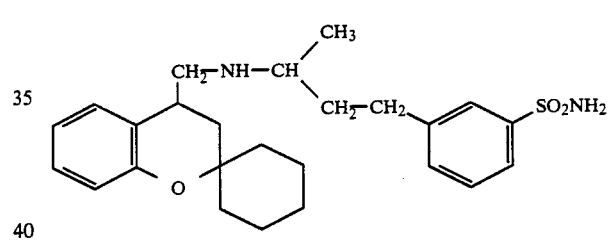
Oil;
EXAMPLE 24
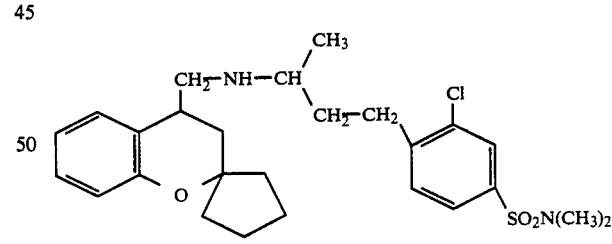
Oil;
EXAMPLE 25
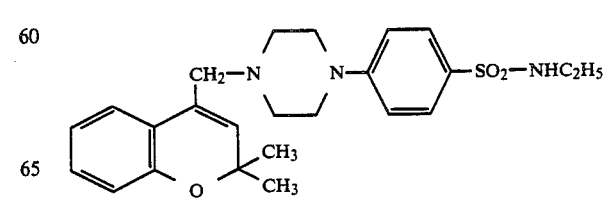
HCl salt; m.p.: 100°–102° C.

EXAMPLE 26
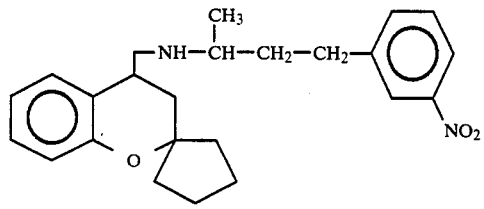
B.p.: 225°–235° C./0.04 mmHg
EXAMPLE 27
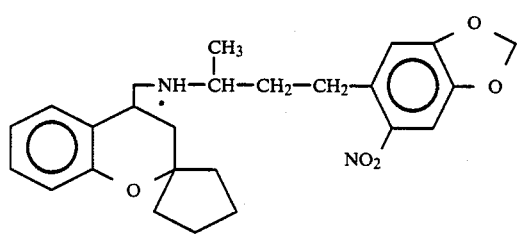
M.p.: 172°–175° C. (fumarate)
EXAMPLE 28
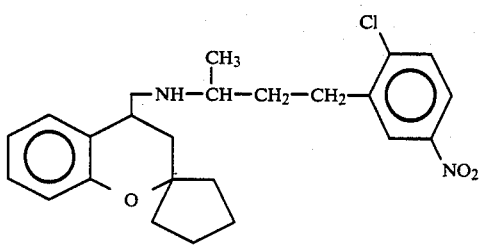
B.p.: 220° C./0.01 mmHg
EXAMPLE 29
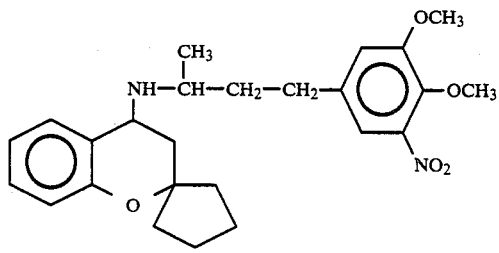
B.p.: 240° C./0.01 mmHg
EXAMPLE 30
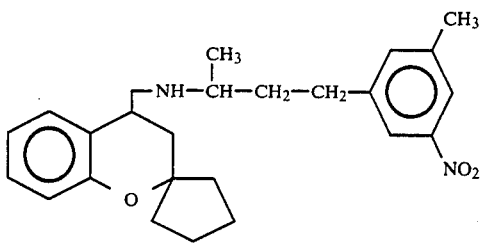
B.p.: 245°–250° C./0.5 mmHg
EXAMPLE 31
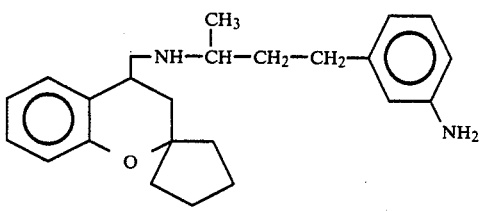
M.p.: 119°–123° C. (maleate)
EXAMPLE 32
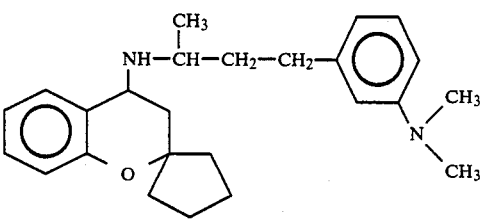
Oil;
EXAMPLE 33
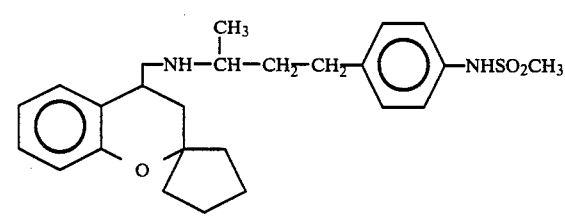
Oil; B.p.: 280° C./0,1 mmHg
EXAMPLE 34
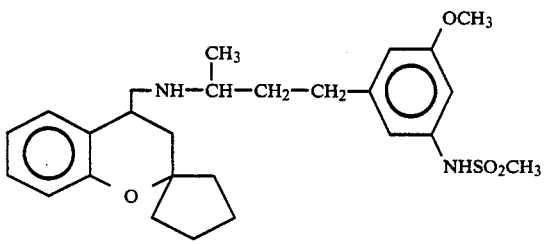
Oil;

EXAMPLE 35
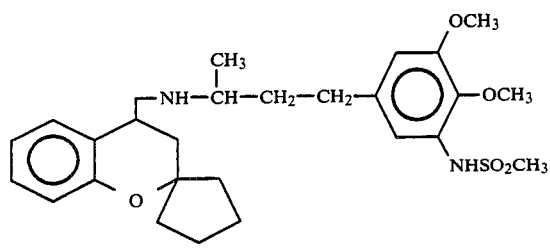
Oil; M.p.: 120°–122° C. (maleate)
EXAMPLE 36
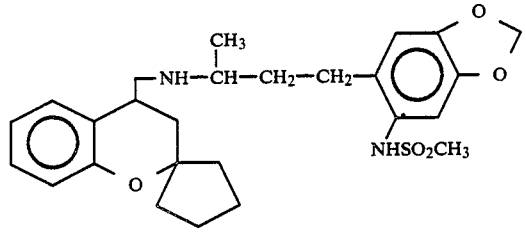
M.p.: 149°–51° C. (maleate)
EXAMPLE 37
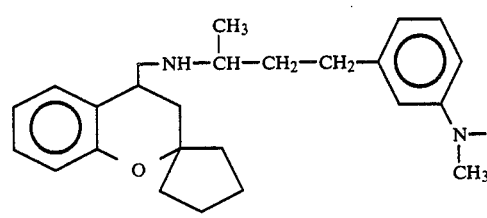
M.p.: 169°–171° C. (decomposition) fumarate
EXAMPLE 38
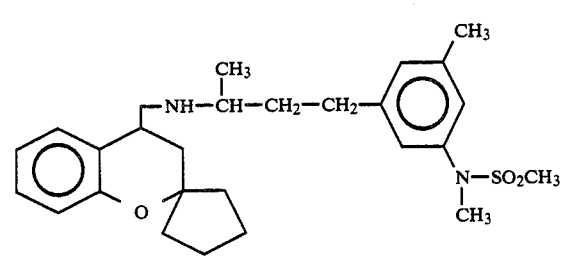
M.p.: 164°–166° C. (maleate)
EXAMPLE 39
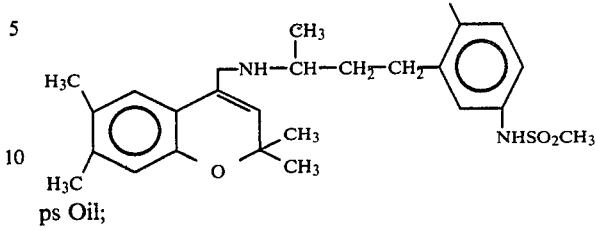
ps Oil;
EXAMPLE 40
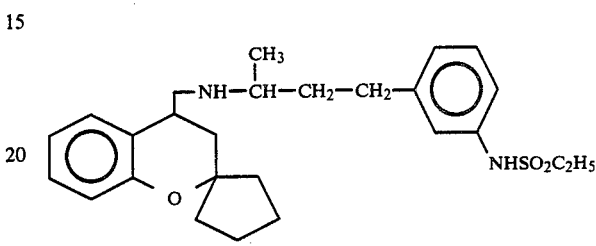
M.p.: 120°–124° C. (decomposition, fumarate)
EXAMPLE 41
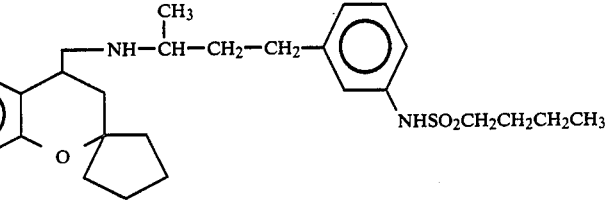
M.p.: 119°–120° C. (decomposition, fumarate)
EXAMPLE 42
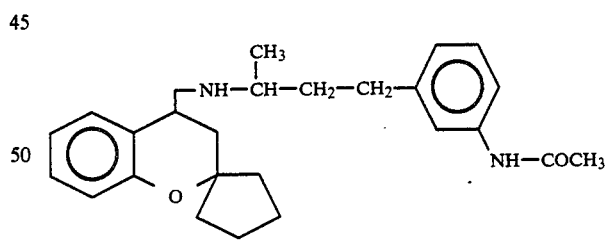
Oil; B.p.: 225° C./0,1 mmHg
EXAMPLE 43
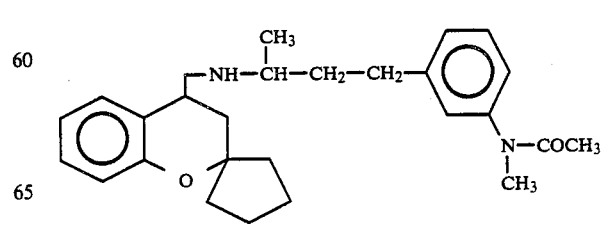
Oil;

EXAMPLE 44
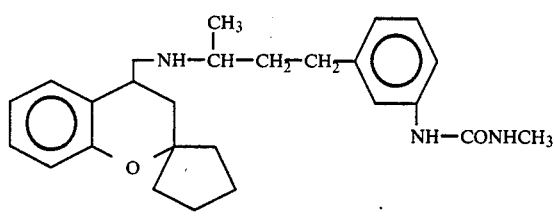
Oil;
EXAMPLE 45
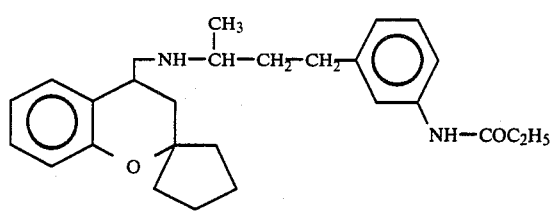
M.p.: 132° C. (decomposition, fumarate)
EXAMPLE 46
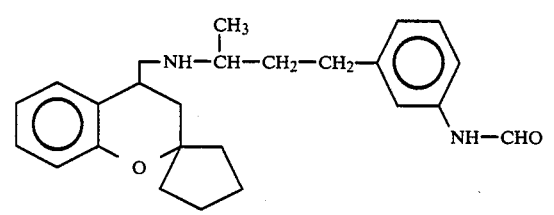
M.p.: 119° C. (decomposition, fumarate)
EXAMPLE 47
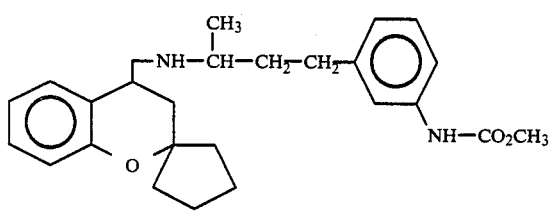
Oil;
EXAMPLE 48
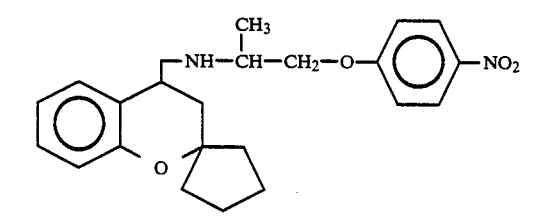
M.p.: 175°–179° C. (maleate)
EXAMPLE 49
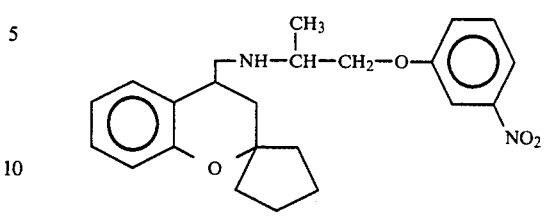
M.p.: 145°–150° C. (maleate)
EXAMPLE 50
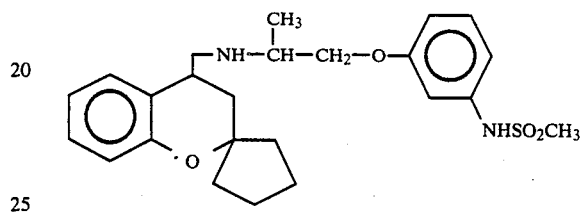
Oil;
EXAMPLE 51
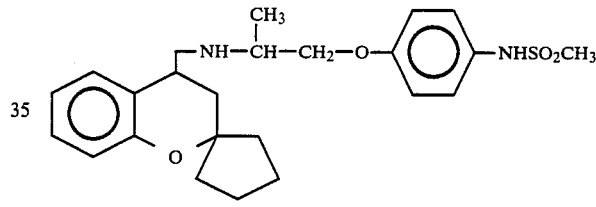
M.p.: 153°–155° C. (maleate)
EXAMPLE 52
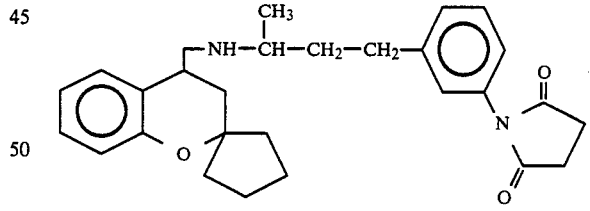
Oil; B.p.: 280°–300° C./0,1 mmHg
EXAMPLE 53
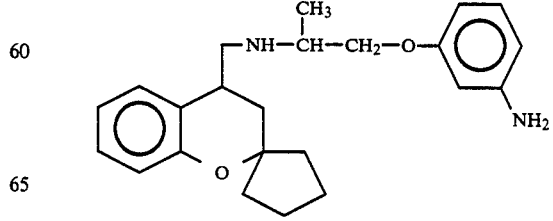
Oil;

EXAMPLE 54
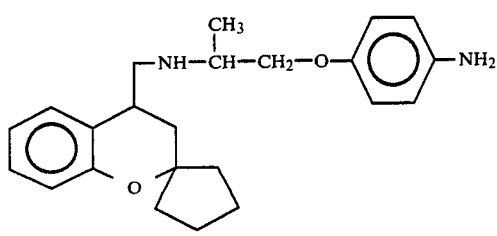
Oil;
EXAMPLE 55
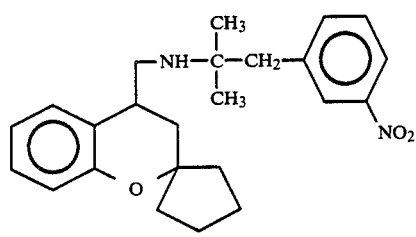
Oil;
EXAMPLE 56
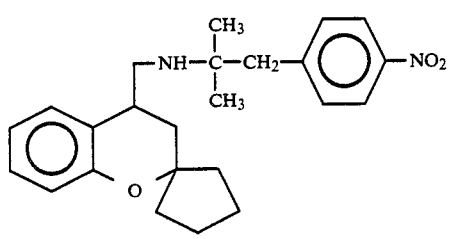
Oil;
EXAMPLE 57
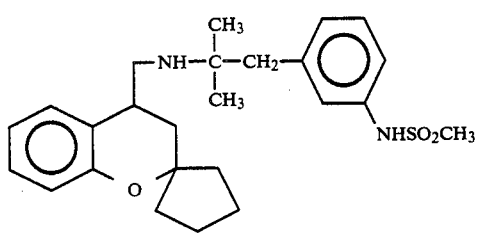
Oil;
EXAMPLE 58
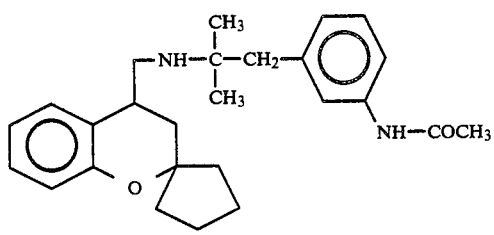
Oil;
EXAMPLE 59
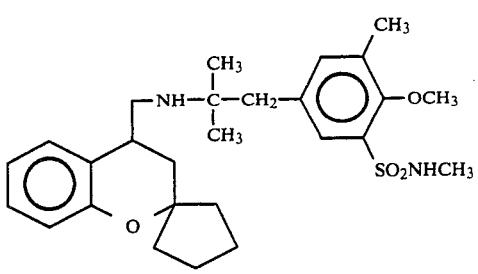
Oil;
EXAMPLE 60
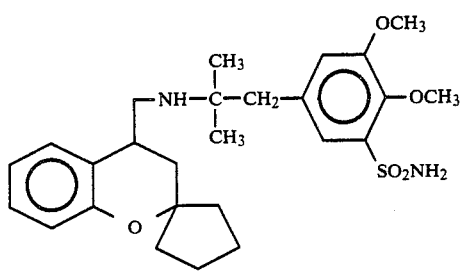
Oil;
EXAMPLE 61
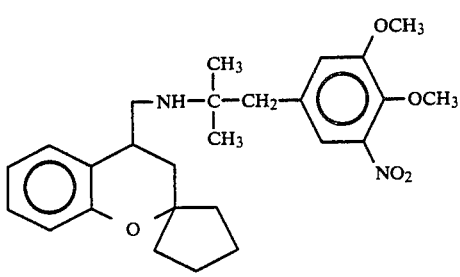
Oil;
EXAMPLE 62
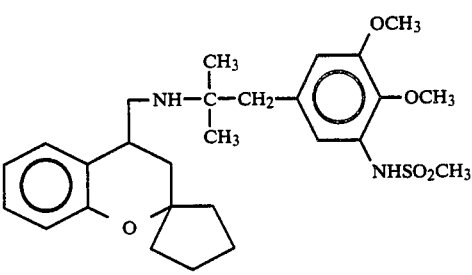
Oil;

EXAMPLE 63

Oil;

EXAMPLE 64

Oil;

EXAMPLE 65

Oil

It will be understood that the specification and examples are illustrative but not limitative of the present invention and that other embodiments within the spirit and scope of the invention will suggest themselves to those skilled in the art.

We claim:

1. A substituted benzopyran of the formula in which

A represents a single bond or double bond, $R_1$ and $R_2$ are identical or different and represent hydrogen, $C_1$–$C_6$-alkyl, $C_5$–$C_7$-cycloalkyl, phenyl, which can be unsubstituted or monosubstituted or disubstituted by $C_1$–$C_4$-alkyl, halogen and/or $C_1$–$C_4$-alkoxy, or, $C_7$–$C_9$-phenylalkyl, the phenyl radical of which is unsubstituted or monosubstituted or disubstituted by $C_1$–$C_4$-alkyl, halogen and/or $C_1$–$C_4$-alkoxy, or $R_1$ and $R_2$, together with the included C atom of the chroman ring, form a 4- to 7-membered saturated carbocyclic ring;

$R_3$ to $R_6$ are identical or different and represent hydrogen, hydroxyl, halogen, $C_1$–$C_6$-alkyl, $C_5$–$C_7$-cycloalkyl, phenyl, which is unsubstituted or monosubstituted by or disubstituted by $C_1$–$C_4$-alkyl, halogen and/or $C_1$–$C_4$-alkoxy, or $C_7$–$C_9$-phenylalkyl, the phenyl radical of which is unsubstituted or monosubstituted or disubstituted by $C_1$–$C_4$-alkyl, halogen and/or $C_1$–$C_4$-alkoxy;

$R_7$, $R_8$, $R_9$, $R_{10}$ and $R_{11}$ are identical or different and represent hydrogen or $C_1$–$C_6$-alkyl, X represents a single bond or methylene which is unsubstituted or monosubstituted or disubstituted by $C_1$–$C_4$-alkyl, or represents oxygen or —$NR_{17}$, wherein $R_{17}$ represents hydrogen or $C_1$–$C_4$-alkyl, or $R_{17}$ together with $R_7$ forms a $C_2$-alkylene bridge, $R_{12}$, $R_{13}$, $R_{14}$, $R_{15}$ and $R_{16}$ each independently represents hydrogen, hydroxyl, chlorine, fluorine, alkyl having 1–4C atoms, alkoxy having 1 to 3C atoms, phenylalkoxy having up to 8C atoms or trifluoromethyl, and one or two of these substituents each independently represents nitro, cyano or the $$\mathrm{N}\!\!\begin{array}{c}R_{18}\\ \diagdown\\ COR_{21}\end{array},\ \mathrm{N}\!\!\begin{array}{c}R_{18}\\ \diagdown\\ SO_2R_{20}\end{array},\ \mathrm{N}\!\!\begin{array}{c}R_{18}\\ \diagdown\\ R_{19}\end{array},\ CON\!\!\begin{array}{c}R_{18}\\ \diagdown\\ R_{19}\end{array}\ or\ SO_2N\!\!\begin{array}{c}R_{18}\\ \diagdown\\ R_{19}\end{array}\ group,$$

wherein $R_{18}$ and $R_{19}$ are identical or different and each represents hydrogen or alkyl having 1–4C atoms which is unsubstituted or monosubstituted to trisubstituted by halogen, $R_{20}$ represents alkyl having 1–6C atoms which is unsubstituted or monosubstituted to trisubstituted by halogen, and $R_{21}$ represents hydrogen, alkyl, alkoxy or alkylamino, each having 1–4C atoms per alkyl and alkoxy group, the alkyl radical being unsubstituted or monosubstituted to trisubstituted by halogen, and $R_{21}$ and $R_{13}$ or $R_{13}$ and $R_{14}$ together optionally represent an alkylenedioxy group having 1 or 2C atoms or the group —CH=CH—CH=CH—, or $R_{18}$ together with $R_{21}$ are a trimethylene or tetramethylene radical, or a pharmaceutically acceptable addition salt thereof.

2. A compound or salt according to claim 1, in which $R_1$ and $R_2$ each independently represents hydrogen or $C_1$–$C_4$-alkyl or $R_1$ and $R_2$, together with the carbon atom between them, form a saturated carboxyclic $C_5$ or $C_6$ ring, $R_3$ and $R_6$ each independently represents hydrogen, hydroxyl, $C_1$–$C_4$-alkoxy or chlorine, $R_7$ to $R_{11}$ each independently represents hydrogen or $C_1$–$C_4$-alkyl, X is single bond, oxygen, methylene or —$NR_{17}$, wherein $R_{17}$ denotes hydrogen or $C_1$–$C_3$-alkyl, or wherein $R_{17}$ together with $R_7$ forms an ethylene bridge, and $R_{12}$ to $R_{16}$ each independently represents hydrogen, chlorine, $C_1$-$C_4$-alkyl, $C_1$-$C_3$-alkoxy, phenylalkoxy having up to 8C atoms or trifluoromethyl, and $R_{12}$ and $R_{13}$ or $R_{13}$ and $R_{14}$ together optionally each form a methylenedioxy group or a —CH=CH—CH=CH— group, and wherein one or two or $R_{12}$ to $R_{16}$ each independently represents nitro, cyano or the

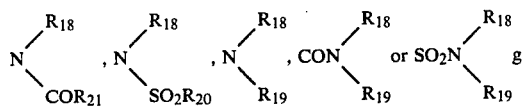

group, wherein $R_{18}$ and $R_{19}$ each independently represents hydrogen or alkyl having 1-4C atoms which is optionally substituted by halogen, and wherein $R_{20}$ represents alkyl having 1-4C atoms which is optionally substituted by fluorine or chlorine, and wherein $R_{21}$ represents hydrogen or alkyl having 1-4C atoms which is optionally substituted by fluorine or chlorine, or represents alkoxy having 1-2C atoms.

3. A compound according to claim 1, wherein such compound is 2,2-spirocyclopentane-4-[N-(3-m-methylsulphonylmethylaminophenyl)-(2-methyl)-2-propyl]-aminomethyl-chroman of the formula

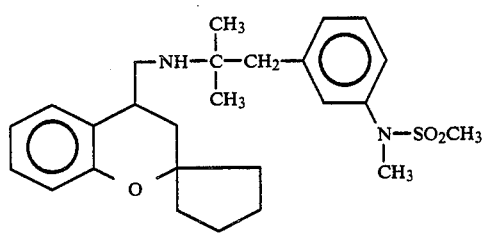

or a pharmaceutically acceptable addition salt thereof.

4. A compound according to claim 1, wherein such compound is 2,2-spirocyclopentane-4-[N-(4-m-methylsulphonylaminophenyl)-2-butyl]-aminomethyl-chroman of the formula

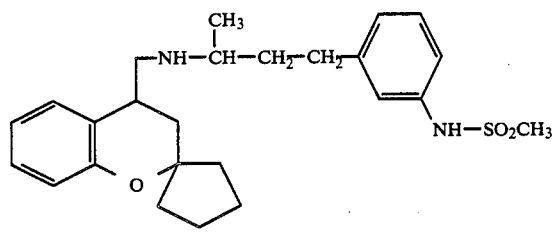

or a pharmaceutically acceptable addition salt thereof.

5. A compound according to claim 1, wherein such compound is 2,2-spirocyclopentane-4-[N-(4-m-methylaminocarbonylphenyl)-2-butyl]-aminomethyl-chroman of the formula

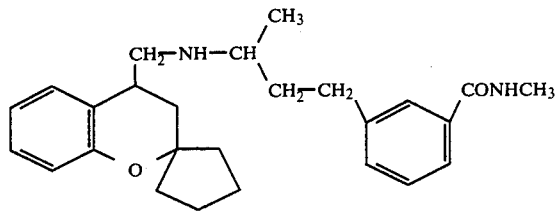

or a pharmaceutically acceptable addition salt thereof.

6. A compound according to claim 1, wherein such compound is 2,2-spirocyclopentane-4-[N-(4-(3-methylaminosulphonyl)-4-methoxy)-phenyl)-2-butyl]-aminomethyl-chroman of the formula

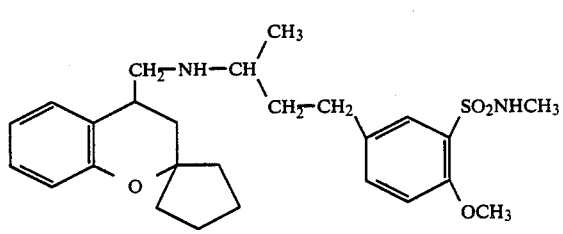

or a pharmaceutically acceptable addition salt thereof.

7. A compound according to claim 1, wherein such compound is 2,2-spirocyclopentane-4-[N-(4-(3-methoxy-5-methylsulphonylamino)-phenyl)-2-butyl]-aminomethyl-chroman of the formula

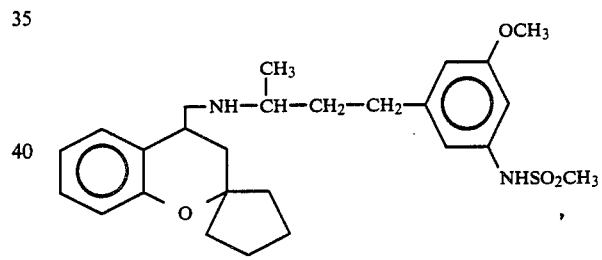

or a pharmaceutically acceptable addition salt thereof.

8. A compound according to claim 1, wherein such compound is 2,2-spirocyclopentane-4-[N-(4-(3,4-dimethoxy-5-methylsulphonylamino)-phenyl)-2-butyl]-aminomethyl-chroman of the formula

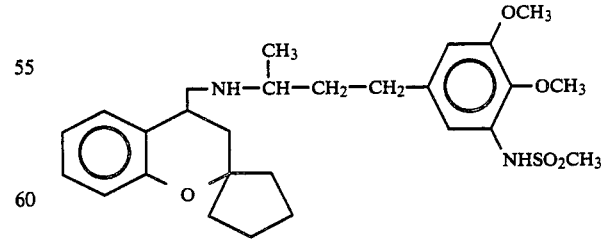

or a pharmaceutically acceptable addition salt thereof.

9. A compound according to claim 1, wherein such compound is 2,2-spirocyclopentane-4-[N-(4-m-methylsulphonylmethylaminophenyl)-2-butyl]-aminomethyl-chroman of the formula

10. A compound according to claim 1, wherein such compound is 2,2-spirocyclopentane-4-[N-(4-(3-methyl-5-methylsulphonyl-methylamino)-phenyl)-2-butyl]-aminomethyl-chroman of the formula

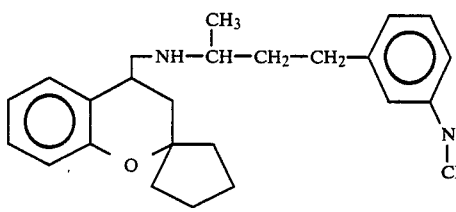

or a pharmaceutically acceptable addition salt thereof.

11. A compound according to claim 1, wherein such compound is 2,2-spirocyclopentane-4-[N-(3-m-methylsulphonylaminophenyl)-(2-methyl)-2-propyl]-aminomethyl-chroman of the formula

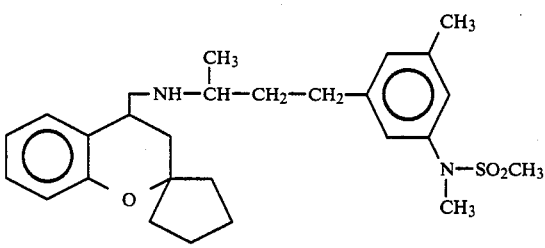

or a pharmaceutically acceptable addition salt thereof.

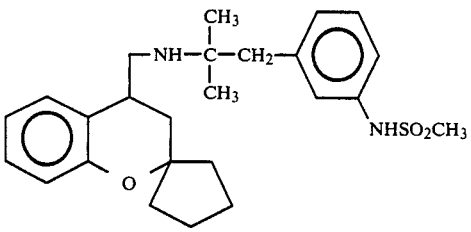

or a pharmaceutically acceptable addition salt thereof.

12. An anti-hypertensive composition comprising an amount effective therefor of a compound or salt according to claim 1 in admixture with a diluent.

13. A unit dose of a composition according to claim 12 in the form of a tablet, ampule or capsule.

14. A method of lowering the blood pressure of a patient which comprises administering to a patient in need thereof an anti-hypertensive effective amount of a compound or salt according to claim 1.

15. The method according to claim 14, wherein such compound is
2,2-spirocyclopentane-4-[N-(4-m-methylsulphonylaminophenyl)-2-butyl]-aminomethyl-chroman,
2,2-spirocyclopentane-4-[N-(4-m-methylaminocarbonylphenyl)-2-butyl]-aminomethyl-chroman,
2,2-spirocyclopentane-4-[N-(4-(3-methylaminosulphonyl-4-methoxy)-phenyl)-2-butyl]-aminomethyl-chroman,
2,2-spirocyclopentane-4-[N-(4-(3-methoxy-5-methylsulphonylamino)-phenyl)-2-butyl]-aminomethyl-chroman,
2,2-spirocyclopentane-4-[N-(4-(3,4-dimethoxy-5-methylsulphonylamino)-phenyl)-2-butyl]-aminomethyl-chroman,
2,2-spirocyclopentane-4-[N-(4-m-methylsulphonyl-methylaminophenyl)-2-butyl]-aminomethyl-chroman,
2,2-spirocyclopentane-4-[N-(4-(3-methyl-5-methylsulphonylmethylamino)-phenyl)-2-butyl]-aminomethyl-chroman,
2,2-spirocyclopentane-4-[N-(3-m-methylsulphonylaminophenyl)-(2-methyl)-2-propyl]-aminomethyl-chroman,
2,2-spirocyclopentane-4-[N-(3-m-methylsulphonylmethylaminophenyl)-(2-methyl)-2-propyl]-aminomethylchroman,
or a pharmaceutically acceptable addition salt thereof.

* * * * *

UNITED STATES PATENT AND TRADEMARK OFFICE
CERTIFICATE OF CORRECTION

PATENT NO. : 4,659,737

DATED : April 21, 1987

INVENTOR(S) : Hans-Joachim Kabbe, et al.

It is certified that error appears in the above-identified patent and that said Letters Patent is hereby corrected as shown below:

| | |
|---|---|
| Title Page, under "Foreign Patent Documents" | Delete "7/1984" and substitute --5/1984-- |
| Col. 1, line 46 | After "$C_3$" insert -- - -- |
| Col. 4, line 36 | After fourth formula insert --,-- |
| Col. 7, line 8 | Delete "hydroxide" first instance and substitute --hydroxides-- |
| Col. 8, line 15 | Correct spelling of --spirocyclopentachroman-- |
| Col. 9, line 1 | After "4" second instance insert -- - -- |
| Col. 9, line 24 | Delete "eliminates" and substitute --eliminate-- |
| Col. 12, line 26 | After "3" insert -- - -- |
| Col. 13, line 8 | After "2" insert -- - -- |
| Col. 13, line 12 | Delete "spiro-cyclopentachromene" and substitute --spirocyclopentachromene-- |
| Col. 15, line 47 | Correct spelling of --precipitate-- |
| Col. 9, line 50 | Delete end of first structure and substitute |

UNITED STATES PATENT AND TRADEMARK OFFICE
CERTIFICATE OF CORRECTION

PATENT NO. : 4,659,737

DATED : April 21, 1987

INVENTOR(S) : Hans-Joachim Kabbe, et al.

It is certified that error appears in the above-identified patent and that said Letters Patent is hereby corrected as shown below:

Col. 24, line 12    Before "Oil" delete "ps"

Col. 30, line 50    Delete "$R_{21}$" and substitute --$R_{12}$--

Signed and Sealed this

Fifteenth Day of December, 1987

Attest:

DONALD J. QUIGG

*Attesting Officer*  *Commissioner of Patents and Trademarks*